United States Patent [19]

Jung et al.

[11] Patent Number: 4,931,471
[45] Date of Patent: Jun. 5, 1990

[54] AMIDES OF PARAMETHOXYCINNAMIC AND UTILIZATION THEREOF AS SOLAR FILTERS

[75] Inventors: Louis Jung, Strasbourg; Dominique Robert, Draguignan, both of France

[73] Assignee: Universite Louis Pasteur, Strasbourg, France

[21] Appl. No.: 252,655

[22] Filed: Oct. 3, 1988

Related U.S. Application Data

[63] Continuation of Ser. No. 939,119, filed as PCT FR86/00108 on Mar. 28, 1986, published as WO86/05783 on Oct. 9, 1986, abandoned.

[30] Foreign Application Priority Data

Mar. 28, 1985 [FR] France ................... 85 04898

[51] Int. Cl.$^5$ .................. A61K 31/165; C07C 103/84
[52] U.S. Cl. ................... 514/622; 514/352; 514/377; 514/472; 546/309; 548/233; 549/480; 564/170
[58] Field of Search ............... 564/170; 548/344, 215, 548/200, 540, 342, 233; 544/391; 514/622, 374, 365, 255, 423, 400, 352, 377, 472; 549/480; 546/309

[56] References Cited

U.S. PATENT DOCUMENTS 4,252,804  2/1981  Joullié et al. ............... 514/427 X

FOREIGN PATENT DOCUMENTS 2015447 10/1970 Fed. Rep. of Germany ...... 564/182
2932923  2/1981 Fed. Rep. of Germany ...... 548/342
2204628  5/1914 France ........................... 548/342
8410009  6/1984 France ........................... 562/426
2545355 11/1984 France ........................... 562/471

OTHER PUBLICATIONS

*Grant and Hackh'3 s Chemical Dictionary*, 5th Ed., McGraw Hill, New York, 1967, p. 491.
March, J., *Advanced Organic Chemistry*, McGraw Hill, New York, 1968, pp. 335, 319, 356, 347.
*Chemical Abstracts*, 59:7316h (1963), [Japan 18, 098, 11/16/62].
*Chemical Abstracts*, vol. 94:57968s (1981) [Li, R. et al., *Pei-Ching I Hsuem Yuan Hsuem Pao* 1980, 12(3), 153–157].
*Chemical Abstracts*, vol. 73:96092m (1970) [Pousset, J. et al., *Bull. Soc. Chim. Biol.* 1970, 52(4), 450–452].

*Primary Examiner*—Richard A. Schwartz
*Attorney, Agent, or Firm*—Browdy and Neimark

[57] ABSTRACT

Derivatives with amide function obtained by reaction between derivatives of linear, branched or cyclic amines having an amino acid or peptidic structure and paramethoxycinnamic acid or urocanic acid. Application of said compounds as specific solar filter, absorbing about 310 nm and avoiding erythematous phenomena during exposures to the sun and as active principles of dermo-pharmaceutical and cosmetological preparations.

9 Claims, No Drawings

AMIDES OF PARAMETHOXYCINNAMIC AND UTILIZATION THEREOF AS SOLAR FILTERS

This application is a continuation of application Ser. No. 939,119, filed as PCT FR86/00108 on Mar. 28, 1986, published as WO86/05783 on Oct. 9, 1986, now abandoned.

The present invention relates to novel derivatives of paramethoxycinnamic acid and urocanic acid and to the preparation of the said derivatives. The invention also relates to the cosmetological use and the protection of human skin from solar radiation. It further relates to the dermo-pharmaceutical and cosmetic compositions in which the said derivatives are present.

The paramethoxycinnamic acid derivatives currently used as solar filters and present in cosmetological compositions as the active ingredient correspond to the following formula I:

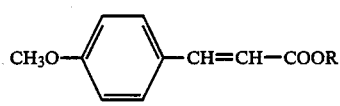

R representing alkyl groups which may carry sulfur-containing functional groups (cf. French Patent Application No. 84 10009 of 22 June 1984).

The best-known compound of the formula I corresponds to the formula Ibis below:

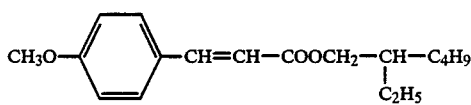

This compound has a number of disadvantages which are common to all the solar filters in use at the present time:
weak adhesion to the skin (elimination when bathing in the sea or perspiring);
passage into the blood when used by man;
in view of this weak adhesion, several applications are necessary (every 2 to 3 hours), causing renewed penetration into the blood on each application;
the product hydrolyzes to p-methoxycinnamic acid under the influence of the esterases in the skin and plasma, thereby losing the desired UV-B filtering power on the skin.

The above-mentioned French patent application also describes novel solar filters with a sulfur-containing and/or amino acid structure which carry an ester functional group. The UV-B filtering power of these compounds is identical to or greater than that of the compounds of the formula I above.

The inventors were also able to demonstrate that, in contrast to the compounds of the formula I, these novel solar filters attached themselves to the surface of the epidermis, the proof having been obtained using rabbits as the experimental model: rabbit skin is in fact considerably more permeable than human skin and allows a better quantification of the solar filter or its metabolite in the blood (GC/MS method of quantitative analysis permitting specific quantitative determinations of the order of ng/ml). For some pharmaceutical formulations of products of the formula I, up to 10-20% of the solar filter applied is found in the blood (D. Claus, University doctoral thesis, Strasbourg 1982: FIG. 1).

As far as the sulfur-containing esters were concerned, no trace of solar filter or metabolite was found in the rabbit's blood.

However, the inventors were able to demonstrate that part of the ester functional group is hydrolyzed under the influence of the esterases in the skin, using a sample of previously shaved skin from the abdomen of a rat. The hypodermis was carefully detached by means of a razor blade. The remaining epidermis and dermis were cut into thin lamellae and placed in a conical flask containing 20 ml of phosphate buffer of pH 8. The lamellae were then ground in a Potter mill with large teeth so as to prevent the proteases from being released from the cell nuclei. The preparation obtained was centrifuged at 25,000 rpm and the supernatant was removed. 10 μmol of the test product were suspended in 4 ml of the homogenate. After 12 h, the solutions were analyzed by TLC.

The solar filter consisting of a sulfur-containing ester is totally hydrolyzed after 12 h. However, it should be noted that the esterase reactivity of skin homogenates (which is not of microbial origin) is much greater than that of normal skin; in the case of whole cells, the esterases are localized especially inside the cells. Nevertheless, this type of enzyme is released at the moment of keratinization, i.e. on the surface of the skin (J. Wepierre, Labo-Pharma, Probl. Tech. 1983, 31, 730-734).

It is also known to use urocanic acid, of the formula II below, as a solar filter:

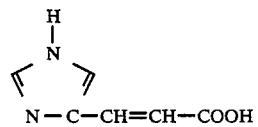

In this case, however, one is again confronted with the problems, described above, of weak adhesion to the skin and passage into human blood.

The object of the present invention is consequently to provide chromophoric derivatives of the paramethoxycinnamic and urocanic types which satisfy practical needs better than the solar filters consisting of known derivatives of paramethoxycinnamic acid and urocanic acid, especially in so far as the novel derivatives have a greater chemical stability than the known derivatives when used as solar filters, and a greater adhesion to the skin when applied thereto, and in so far as these novel derivatives, and any metabolites thereof, are retained on the epidermis and do not pass into the blood.

The present invention relates to novel amides of paramethoxycinnamic acid and urocanic acid which correspond to the general formula A—CH=CH—CO—B wherein A and B are selected so that the general formula corresponds to compounds of the formulae III and IV below:

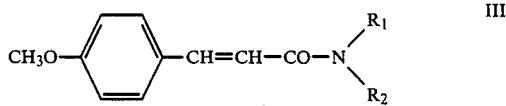

-continued

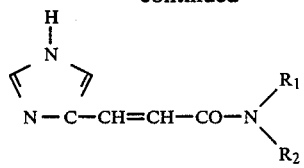
IV in which:
the ethylenic double bonds can exist either in the trans form or in the cis form, and
$R_1$ and $R_2$ can be hydrogen, an alkyl group or an aryl group, with the proviso that $R_1$ is not a hydrogen atom when $R_2$ is an alkyl group,
$R_1$ and $R_2$ can form, with the nitrogen atom, a substituted or unsubstituted heterocyclic cycloalkyl group other than piperidine,
$R_1$ or $R_2$ can also be a group of the formula:

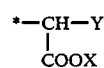

where X and Y can be an alkyl group or an aryl group,

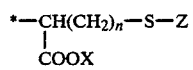

where Z can be hydrogen, an alkyl group or an aryl group and where n is an integer between 1 and 6 but preferably 1 or 2, or

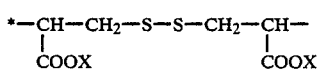

to which two molecules of filter chromophores of the paramethoxycinnamic acid or urocanic acid type are attached,

can be a urocanic acid derivative of the type:

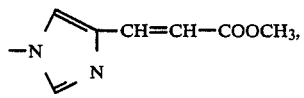

or

can be a peptide structure comprising two or more amino acids in which the terminal or branched acid or amine functional groups can be free or part of ester or amide groups, provided that, in the case of the compounds of the formula IV, the peptide structure is other than that of a salt.

In the present context, the term "alkyl" denotes aliphatic hydrocarbon groups containing 1 to 12 carbon atoms and having a linear or branched chain. Preference is given to lower alkyl groups, i.e. alkyl groups containing 1 to 4 carbon atoms.

The term "aryl" denotes non-heterocyclic aromatic groups of the phenyl or benzyl type and higher homologs, which may or may not be substituted, and heterocyclic aromatic groups having 4 to 7 carbon atoms in the aromatic ring and 1 to 4 heteroatoms, which can be oxygen, nitrogen or sulfur, of the furan, pyridine or oxazole type.

The term "heterocyclic cycloalkyl" denotes the saturated derivatives of heterocyclic aromatic groups, of the piperidine, piperazine, oxazolidine, thiazolidine or pyrrolidine type.

In an advantageous embodiment of the novel derivatives according to the invention, the group:

represents a linear, branched or cyclic primary or secondary amine, or it can be a peptide not containing sulfur, of the L-tyrosine or L-histidine type, or it can represent a sulfur-containing amino acid or peptide of the methionine, cysteine, S-methylcysteine, S-benzylcysteine, cystine or oxidized or unoxidized glutathione type, or it can represent a peptide of tyrosine/glutamic acid structure, or alternatively trans-urocanic acid.

The present invention also relates to a process for the preparation of the novel amides according to the present invention, which consists in reacting paramethoxycinnamoyl chloride or the hydrochloride of urocanoyl chloride with an amine or with an amine of an amino acid ester or of a peptide which may or may not contain sulfur.

In one embodiment of the process for the preparation of the amides according to the present invention, the acid chloride is prepared by reacting thionyl chloride with the acid in an organic solvent, and a compound carrying a primary or secondary amine functional group is then reacted with the said acid chloride in an organic solvent, in the presence of triethylamine.

The present invention further relates to solar filters in which the active constituent is an amide of the formulae III and/or IV above.

The invention also relates to dermo-pharmaceutical or cosmetological compositions in which the active constituent is an amide of the formulae III and/or IV above, in association with a suitable vehicle.

Such compositions, which can advantageously be formulated as emulsions or sprays, are particularly useful for the treatment of photodermatosis.

The literature describes a variety of p-methoxycinnamic acid amides which can be used as agents for protecting against sunstroke; in particular, CHEMICAL ABSTRACTS Vol. 59, no. 7, 30 September 1963, describes compounds of the formula p-MeOC$_6$H$_4$CH=CHCONX(CH$_2$)$_n$Y in which X is hydrogen or a lower alkyl, Y is a hydroxyl or acid group and n is equal to 1 or 2, and specifically p-methoxycinnamoylsarcosine. Urocanic acid amides capable of absorbing ultraviolet light are also known, especially the stearylamide and dodecylamide of urocanic acid (cf.

CHEMICAL ABSTRACTS Vol. 84, no. 22, 31 May 1976, page 346, no. 155513c, and French Patent No. 2 204 628 to Ajinomoto). However, there is no mention of whether or not the amides described could constitute a filter absorbing UV-A and UV-B simultaneously or nonsimultaneously, or whether or not they could enter the blood through the dermo-epidermal barrier.

By contrast, the p-methoxycinnamic acid amides and urocanic acid amides of the above formulae III and IV according to the invention are solar filters which not only undergo little or almost no degradation due to the action of the enzymes in the skin, but also adhere to the surface of the skin for long periods without being removed by the water when the person is bathing in the sea, for example, or by perspiration, and do not enter the blood circulation through the skin.

The derivatives forming the subject of the invention possess valuable properties as solar filters. They exhibit a maximum efficacy in terms of their ultraviolet absorption capacity. Their absorption spectrum shows an absorption maximum at around 310 nm, which is the zone of the erythemogenic UV-B radiation.

Apart from the above provisions, the invention also includes others which will become apparent from the following description.

The invention will be understood more clearly with the help of the additional description which follows; this refers to embodiments of the process forming the subject of the present invention.

It should be clearly understood, however, that these embodiments are given solely to illustrate the subject of the invention and do not in any way imply a limitation.

EXAMPLES

EXAMPLE I

N-(4-Methoxycinnamoyl)piperidine

First step: Synthesis of paramethoxycinnamoyl chloride 20 g of paramethoxycinnamic acid, 30 g of thionyl chloride and 200 ml of benzene are brought to the boil in a round-bottomed flask fitted with a condenser. After 8 h under reflux, the solvent is evaporated off by means of a rotary evaporator. The residue of thionyl chloride is removed in the same way by being successively evaporated off and taken up with benzene.

Second step: Reaction of the acid chloride with piperidine

In a conical flask, 1.96 g of the paramethoxycinnamoyl chloride are dissolved in 20 ml of benzene. 2 ml of piperidine are added. After evaporation to dryness in vacuo, the residue is taken up in N hydrochloric acid and extracted with chloroform. The chloroform solution is washed successively with a 10% aqueous solution of $KHCO_3$ and with water. It is then collected, dried over magnesium sulfate and evaporated. The product obtained is precipitated in cyclohexane and filtered off. After recrystallization from a 95° ethanol/water mixture (⅓:⅔), 2.15 g of white crystals are isolated (yield=78%).

M.p.=92° C.

UV spectrum ($CHCl_3$): maximum 295 nm.

IR spectrum (KBr): The bands characteristic of the paramethoxycinnamic component and the piperidine component are present together with the amide carbonyl at 1635 $cm^{-1}$.

NMR spectrum ($CDCl_3$): presence of the signals characteristic of both the paramethoxycinnamic and piperidine components.

Chromatographic constant: on a thin layer of MERCK 60F254 silica; single spot: Rf=0.78; developing solvent: benzene/chloroform/methanol (20:10:5):A.

M.W.: 245 (determined by mass spectrometry).

EXAMPLE II

Methyl ester of N-(4-methoxycinnamoyl)-L-methionine

In a conical flask, 1.96 g of paramethoxycinnamoyl chloride are dissolved in 20 ml of benzene in the presence of 2.8 ml of triethylamine. 1.99 g of the methyl ester of L-methionine are added gradually. The mixture obtained is filtered. After evaporation of the filtrate to dryness in vacuo (15 mm Hg), the residue is taken up in N hydrochloric acid and extracted with chloroform. The chloroform solution is washed successively with a 10% aqueous solution of $KHCO_3$ and with water. It is then collected, dried over magnesium sulfate and evaporated. The product obtained is precipitated in cyclohexane and filtered off. After recrystallization from a 95° ethanol/water mixture (1:1), 2.53 g of white crystals are isolated (yield=78%).

M.p.=95° C.

UV spectrum ($CHCl_3$) maximum 309 nm.

IR spectrum (KBr): The bands characteristic of the paramethoxycinnamic component and the L-methionine methyl ester component are present together with the amide carbonyl at 1650 $cm^{-1}$.

NMR spectrum ($CDCl_3$): presence of the signals characteristic of both the paramethoxycinnamic and L-methionine methyl ester components.

Chromatographic constant: single spot: Rf=0.76 (solvent A).

M.W.: 323 (determined by mass spectrometry).

EXAMPLE III

Methyl ester of N-(4-methoxycinnamoyl)-L-cysteine

In a conical flask, 1.96 g of paramethoxycinnamoyl chloride are dissolved in 20 ml of benzene in the presence of 2.8 ml of triethylamine. 1.72 g of the methyl ester of L-cysteine are added gradually. The mixture obtained is evaporated to dryness in vacuo. The residue is taken up in water, stirred for 2 h and filtered off. After recrystallization from a 95° ethanol/water mixture (1:1), 2.21 g of white crystals are isolated (yield=78%).

M.p.=159° C.

UV spectrum ($CHCl_3$): maximum 314 nm.

IR spectrum (KBr): The bands characteristic of the paramethoxycinnamic component and the L-cysteine methyl ester component are present together with the amide carbonyl at 1650 $cm^{-1}$.

NMR spectrum ($CDCl_3$): presence of the signals characteristic of both the paramethoxycinnamic and L-cysteine methyl ester components.

Chromatographic constant: single spot: Rf=0.83 (solvent A).

EXAMPLE IV

Dimethyl ester of N,N'-di(4-methoxycinnamoyl)-L-cystine

In a conical flask, 3.93 g of paramethoxycinnamoyl chloride are dissolved in 20 ml of benzene in the presence of 2.8 ml of triethylamine. 3.41 g of the dimethyl ester of cystine are added gradually.

The product is subsequently synthesized by following the same procedure as that used in Example II. After recrystallization from a 95° ethanol/water mixture (⅔:⅓), 4.46 g of white crystals are isolated (yield=76%).

M.p.=110° C.

UV spectrum (CHCl$_3$): maximum 309 nm.

IR spectrum (KBr): The bands characteristic of the paramethoxycinnamic component and the L-cystine dimethyl ester component are present together with the amide carbonyl at 1650 cm$^{-1}$.

NMR spectrum (CDCl$_3$): presence of the signals characteristic of both the paramethoxycinnamic and L-cystine dimethyl ester components.

Chromatographic constant: single spot: Rf=0.71 (solvent A).

M.W.: 588 (determined by mass spectrometry).

Most abundant ion: 262, corresponding to the cystinyl-paramethoxycinnamic fragment minus sulfur.

EXAMPLE V

Methyl ester of S-methyl-N-(4-methoxycinnamoyl)-L-cysteine

In a conical flask, 1.96 g of paramethoxycinnamoyl chloride are dissolved in 20 ml of benzene in the presence of 2.8 ml of triethylamine. 1.49 g of the methyl ester of S-methyl-L-cysteine are added gradually. The product is subsequently synthesized by following the same procedure as that used in Example II. After recrystallization from a 95° ethanol/water mixture (1:1), 2.28 g of white crystals are isolated (yield=74%).

M.p.=98° C.

UV spectrum (CHCl$_3$): maximum 306 nm.

IR spectrum (KBr): The bands characteristic of the paramethoxycinnamic component and the S-methyl-L-cysteine methyl ester component are present together with the amide carbonyl at 1650 cm$^{-1}$.

NMR spectrum (CDCl$_3$) presence of the signals characteristic of both the paramethoxycinnamic and S-methyl-L-cysteine methyl ester components.

Chromatographic constant: single spot: Rf=0.81 (solvent A).

EXAMPLE VI

Methyl ester of S-benzyl-N-(4-methoxycinnamoyl)-L-cysteine

In a conical flask, 1.96 g of paramethoxycinnamoyl chloride are dissolved in 20 ml of benzene in the presence of 2.8 ml of triethylamine. 2.25 g of the methyl ester of S-benzyl-L-cysteine are added gradually. The mixture obtained is filtered. The filtrate is acidified in the presence of N hydrochloric acid. The benzene solution is collected and rendered alkaline with a 10% aqueous solution of KHCO$_3$. The amide precipitates and is collected by filtration. After recrystallization from a 95° ethanol/water mixture (1:1), 2.61 g of white crystals are isolated yield=68%).

M.p.=128° C.

UV spectrum (CHCl$_3$): maximum 310 nm.

IR spectrum (KBr): The bands characteristic of the paramethoxycinnamic component and the S-benzyl-L-cysteine methyl ester component are present together with the amide carbonyl at 1650 cm$^{-1}$.

NMR spectrum (CDCl$_3$): presence of the signals characteristic of both the paramethoxycinnamic and S-benzyl-L-cysteine methyl ester components.

Chromatographic constant: single spot: Rf=0.63 (solvent A).

EXAMPLE VII

Methyl ester of N-(4-methoxycinnamoyl)-L-tyrosine

In a conical flask, 1.96 g of paramethoxycinnamoyl chloride are dissolved in 20 ml of benzene in the presence of 2.8 ml of triethylamine. 1.95 g of the methyl ester of L-tyrosine are added gradually. The mixture obtained is evaporated to dryness in vacuo. The residue is taken up in water, stirred for 2 h and filtered off. The residue obtained is taken up in a 10% solution of KHCO$_3$, stirred and then extracted with chloroform. The chloroform solution is collected, dried over magnesium sulfate and evaporated. The product obtained is precipitated in cyclohexane and filtered off. After recrystallization from a 95° ethanol/water mixture (1:1), 2.53 g of white crystals are isolated (yield=74%).

M.p.=197° C.

UV spectrum (CHCl$_3$) maximum 312 nm.

IR spectrum (KBr): The bands characteristic of the paramethoxycinnamic component and the L-tyrosine methyl ester component are present together with the amide carbonyl at 1650 cm$^{-1}$.

NMR spectrum (CDCl$_3$): presence of the signals characteristic of both the paramethoxycinnamic and L-tyrosine methyl ester components.

Chromatographic constant: single spot: Rf=0.72 (solvent A).

EXAMPLE VIII

Methyl ester of (4-methoxycinnamoyl)imidazol-4-ylprop-2-enoic acid (amide of paramethoxycinnamic acid and the methyl ester of urocanic acid)

In a conical flask, 1.96 g of paramethoxycinnamoyl chloride are dissolved in 20 ml of benzene in the presence of 2.8 ml of triethylamine. 1.52 g of the methyl ester of urocanic acid are added gradually. The mixture obtained is filtered. The precipitate is taken up in anhydrous acetone and filtered off. The filtrate is evaporated to dryness in vacuo. The residue is taken up in N hydrochloric acid and extracted with chloroform. The chloroform solution is washed successively with a 10% aqueous solution of KHCO$_3$ and with water. It is then collected, dried over magnesium sulfate and evaporated. The product obtained is precipitated in benzene and filtered off. After recrystallization from a 95° ethanol/water mixture (⅔:⅓), 2.14 g of bright yellow crystals are isolated (yield=72%).

M.p.=208° C.

UV spectrum (100° ethanol): maximum 350 nm.

IR spectrum (KBr): The bands characteristic of the paramethoxycinnamic component and the urocanic acid methyl ester component are present together with the amide carbonyl at 1650 cm$^{-1}$.

NMR spectrum (CDCl$_3$+DMSO-d$_6$): presence of the signals characteristic of both the paramethoxycinnamic and urocanic acid methyl ester components.

Chromatographic constant: single spot: Rf=0.61 (solvent A).

EXAMPLE IX

Amide of paramethoxycinnamic acid and the methyl ester of oxidized glutathione

In a conical flask, 393 mg of paramethoxycinnamoyl chloride are dissolved in 20 ml of benzene in the presence of 2.8 ml of triethylamine. 668 mg of the methyl ester of oxidized glutathione are added gradually. The product is subsequently synthesized by following the same procedure as in Example II. After recrystallization from a 95° ethanol/water mixture (1:1), 501 mg of white crystals are isolated (yield=51%).

M.p.=124° C.

UV spectrum (CHCl$_3$): maximum 309 nm.

IR spectrum (KBr): The bands characteristic of the paramethoxycinnamic component and the oxidized glutathione methyl ester component are present.

NMR spectrum (CDCl$_3$): presence of the signals characteristic of both the paramethoxycinnamic and oxidized glutathione methyl ester components.

Chromatographic constant: Rf=0.57 (solvent A).

Mass spectrometry: chemical ionization; formation of derivatives with Methelute; m/e 536, m/e 537, m/e 538: characteristic ions corresponding to the rupture of the disulfide bridge.

EXAMPLE X

N-[3-(1H-Imidazol-4-yl)-1-oxoprop-2-enyl]piperidine

First step: Synthesis of the hydrochloride of urocanoyl chloride

This compound is synthesized analogously to paramethoxycinnamoyl chloride, in the presence of two mol of thionyl chloride per mol of acid.

Second step: Reaction of the acid chloride with piperidine

In a conical flask, 500 mg of the hydrochloride of the acid chloride, 0.4 ml of triethylamine and 0.6 ml of piperidine are mixed in 20 ml of benzene. After stirring for 15 minutes, the mixture is filtered. The filtrate is evaporated by means of a rotary evaporator. The residue is taken up in 5 ml of anhydrous acetone and filtered off. 100 mg of white crystals are collected (yield=19%).

M.p.=164° C.

UV spectrum (CHCl$_3$): maximum 285 nm.

IR spectrum (KBr): The bands characteristic of the urocanic and piperidine components are present together with the amide carbonyl at 1650 cm$^{-1}$.

NMR spectrum (CDCl$_3$) presence of the signals characteristic of both the urocanic and piperidine components.

Chromatographic constant: Rf=0.33 (solvent A).

EXAMPLE XI

Amide of paramethoxycinnamic acid and the methyl ester of trans-urocanic acid

The amide of the formula:

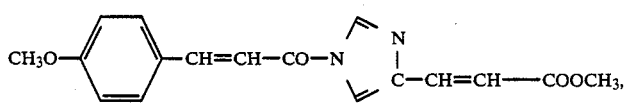

which is capable of absorbing UV-A and UV-B radiation simultaneously, is prepared by following the procedure described in Example VIII.

DERMO-PHARMACEUTICAL COMPOSITION CONTAINING ONE OF THE SOLAR FILTERS FORMING THE SUBJECT OF THE PRESENT INVENTION

The solar filter is incorporated at a concentration of 5% in an emulsion which can have, for example, the following composition:

| | |
|---|---|
| Paraffin | 12 g |
| PEG monostearate and distearate (Tefose 1500) | 7 g |
| Stearic acid | 1 g |
| Cetyl alcohol 0.5 | g |
| Polyethoxylated palmitostearic glyceride (Labrafil M 2130) | 3 g |
| Water | qs 100 g |

When using rat skin homogenates such as those described above, no degradation of the amides according to Examples I and III to XI was observed, whereas the amide of Example II undergoes 30% degradation.

Consequently, with the exception of N-(4-methoxycinnamoyl)-L-methionine, which is slightly degraded by the enzymes in the skin, the amides according to the invention are stable on the surface of the skin.

As is apparent from the foregoing text, the invention is in no way limited to those methods of implementation, embodiments and methods of application which have now been described more explicitly; on the contrary, it encompasses all the variants thereof which may occur to those skilled in the art, without deviating from the framework or the scope of the present invention.

What is claimed is:

1. An amide of the formula:

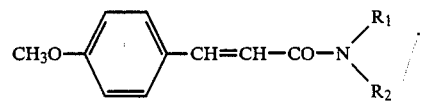

in which:
the ethylenic double bond can exist either in the trans form or in the cis form;
R$_1$ individually represents hydrogen, and
R$_2$ individually represents:
an aryl group,
a group of the formula:

where X and Y can be an alkyl group or an aryl group,
a group of the formula

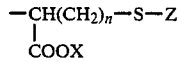

where Z can be hydrogen, an alkyl group or an aryl group and where n is an integer between 1 and 6, or a group of the formula;

to which two molecules of filter chromophores of the paramethoxycinnamic acid are attached; or

can be a peptide structure comprising two or more amino acids in which the terminal or branched acid or amine functional groups can be free or part of ester or amide groups;

wherein said alkyl groups have 1–12 carbon atoms, and said aryl groups are substituted or unsubstituted benzyl or phenyl groups or homologs thereof, or furanyl, pyridinyl, or oxazolyl groups.

2. Amide as claimed in claim 1, wherein

represents an amino ester or peptide radical not containing sulfur, of the L-tyrosine or L-histidine type.

3. Amide as claimed in claim 1, wherein

represents a sulfur-containing amino ester or peptide radical of the methionine, cysteine, S-methylcysteine, S-benzylcysteine, cysteine, glutathione or oxidized glutathione type.

4. Amide of claim 1, wherein

represents a peptide of tyrosine/glutamic acid structure.

5. An amide in accordance with claim 1, wherein $R_2$ represents a group of the formula $$-\underset{\underset{COOX}{|}}{CH}-Y.$$

6. A therapeutic method for protecting human skin from solar radiation, comprising the step of topically applying to skin of a human who is in need of said therapy a therapeutic amount of an amide of the formula

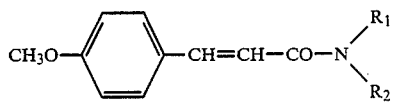

in which:
the ethylenic double bond can exist either in the trans form or in the cis form;
$R_1$ individually represents hydrogen; and
$R_2$ individually represents:
an aryl group,
a group of the formula:

where X and Y can be an alkyl group or an aryl group,
a group of the formula:

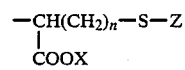

where Z can be hydrogen, an alkyl group or an aryl group and where n is an integer between 1 and 6, or
a group of the formula:

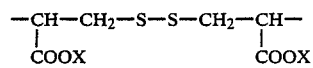

to which two molecules of filter chromophores of the paramethoxycinnamic acid are attached; or

can be a peptide structure comprising two or more amino acids in which the terminal or branched acid or amine-functional groups can be free or part of ester or amide groups;

wherein said alkyl groups have 1–12 carbon atoms, and said aryl groups are substituted or unsubstituted benzyl or phenyl groups or homologs thereof, or furanyl, pyridinyl, or oxazolyl groups.

7. The method of claim 6, wherein

represents a sulfur-containing amine ester radical or peptide of the methionine, cysteine, S-methylcysteine, S-benzylcysteine, cystine, glutathione or oxidized glutathione type.

8. The method of claim 6 wherein $R_2$ represents a group of the formula

9. The method of claim 6, wherein 
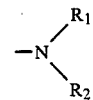
represents a sulfur-containing amino ester radical or peptide of the methionine, cysteine, S-methylcysteine, S-benzylcysteine, cystine, glutathione or oxidized glutathione type.
* * * * *